United States Patent [19]
Zinger

[11] Patent Number: 5,810,885
[45] Date of Patent: Sep. 22, 1998

[54] DEVICE FOR APPLYING ONE OR SEVERAL FLUIDS

[76] Inventor: Freddy Zinger, 29 Kazan Street, 43611 Raanana, Israel

[21] Appl. No.: 860,488

[22] PCT Filed: Dec. 23, 1995

[86] PCT No.: PCT/EP95/05120

§ 371 Date: Jun. 27, 1997

§ 102(e) Date: Jun. 27, 1997

[87] PCT Pub. No.: WO96/19940

PCT Pub. Date: Jul. 4, 1996

[30] Foreign Application Priority Data

Dec. 28, 1994 [EP] European Pat. Off. ............. 94120806

[51] Int. Cl.⁶ .................................................. A61B 17/04
[52] U.S. Cl. ........................... 606/213; 604/82; 604/197; 604/240
[58] Field of Search ................ 604/82, 213, 43, 604/48, 187, 197, 239, 240, 243

[56] References Cited

U.S. PATENT DOCUMENTS

| 4,424,913 | 1/1984 | Ko .......................................... 220/90.2 |
| 4,874,368 | 10/1989 | Miller et al. .............................. 604/82 |
| 4,898,460 | 2/1990 | Magninat et al. ...................... 351/114 |

*Primary Examiner*—Gary Jackson
*Attorney, Agent, or Firm*—Birch, Stewart, Kolasch & Birch, LLP

[57] ABSTRACT

The device for applying one or several fluids, particularly a multi-component fluid, such as medical tissue or dental adhesives, comprises a head piece (9) having channels (25 to 28) for each fluid extending from an inlet side of the head piece (9) to a connection site of the head piece (9). The tubular body (10) comprises an inlet end facing the connection site of the head piece (9) and an outlet end facing away from the inlet end. The tubular body (10) comprises an outer wall, which, at least sectionally, is configured such that the tubular body (10) is plastically deformable, particularly plastically bendable.

6 Claims, 4 Drawing Sheets

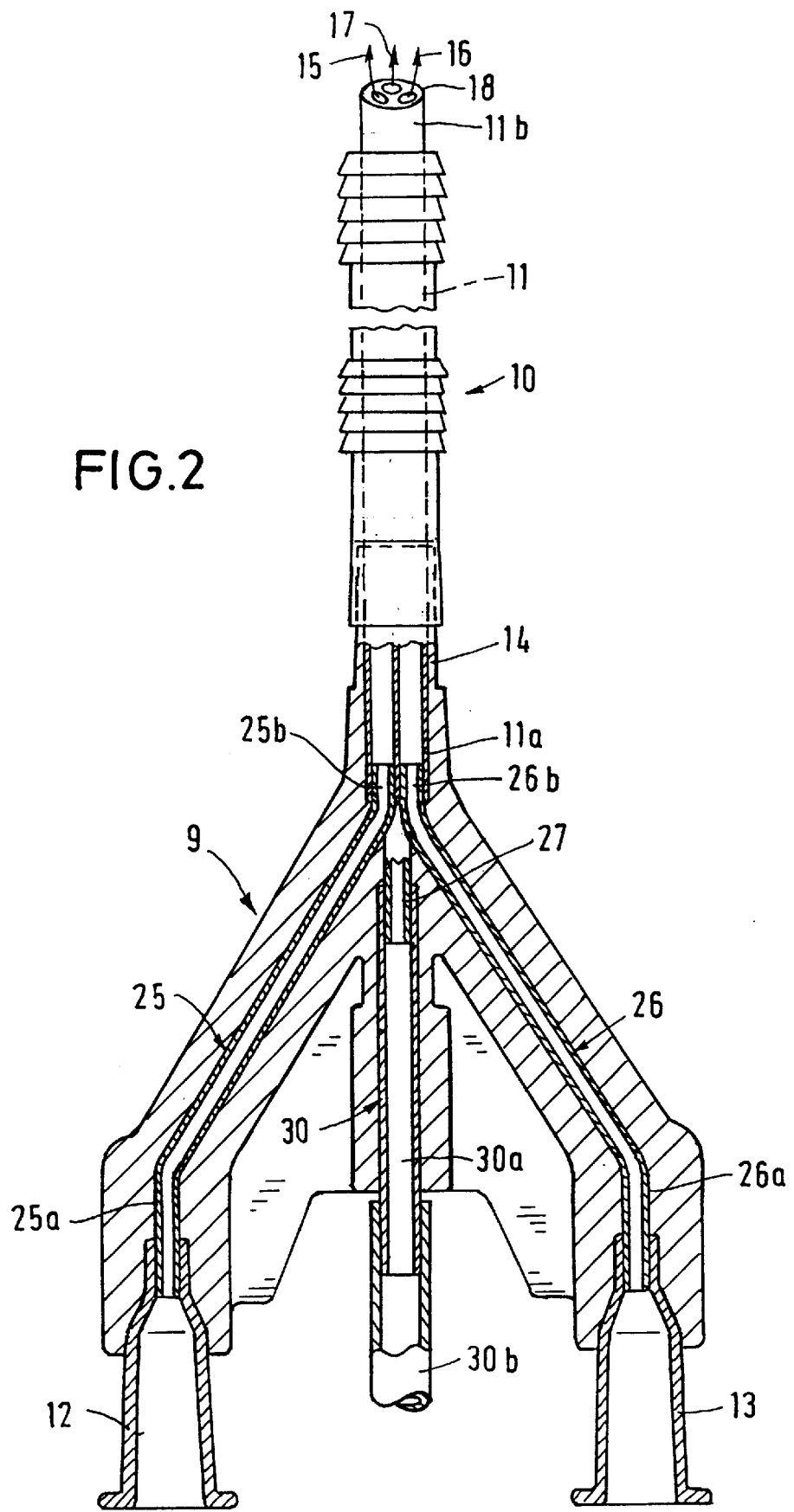

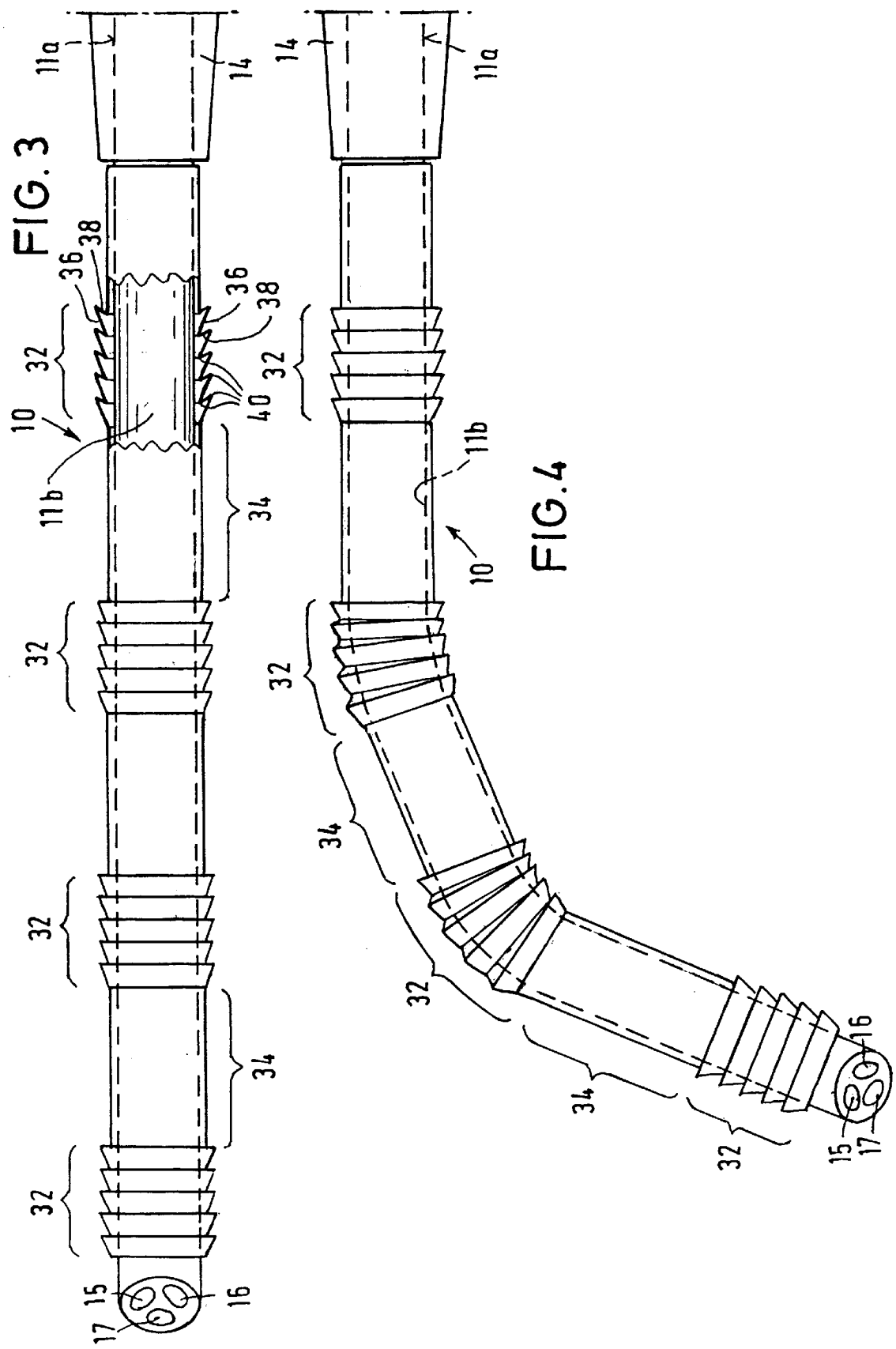

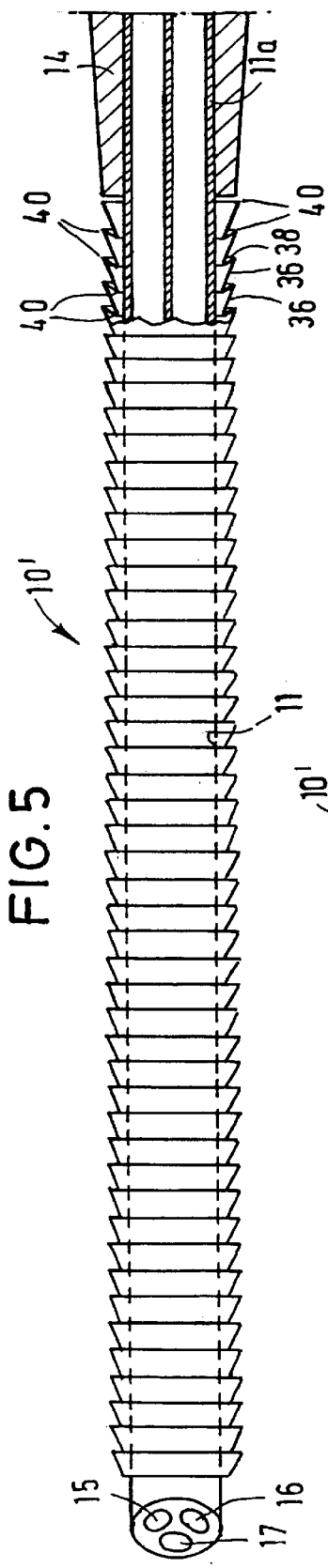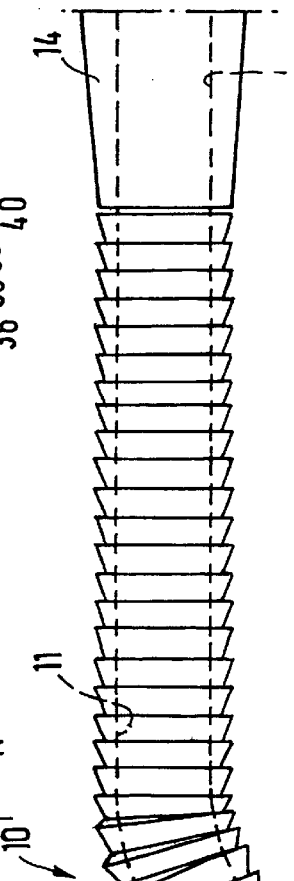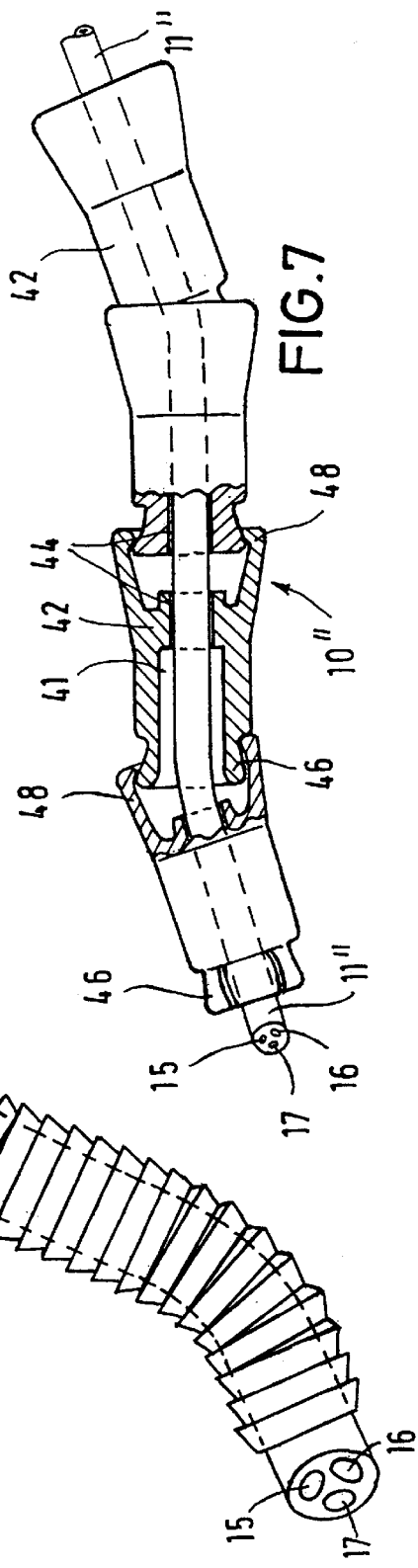

DEVICE FOR APPLYING ONE OR SEVERAL FLUIDS

The invention relates to a device for applying one or several fluids, particularly a multi-component fluid which is, for example, a tissue adhesive or dental adhesive. Such tissue adhesives are used for the seamless or suture-supporting connection of human or animal tissue or organ parts, closing a wound and/or hemostasis. These tissue adhesives comprise several components and are suitably formed by bringing together human or animal proteins and coagulation factors promoting hemocoagulation in situ. To be able to apply the adhesives' components more easily, they are sprayed onto the application site together with a medical gas (oxygen).

BACKGROUND OF THE INVENTION

Application devices of the kind mentioned above are known, for example, from EP 0 037 393 BE, EP 0 210 160 B2, U.S. Pat. No. 4,874,368, DE-OS 42 23 356, and EP 0 315 222 B1. In these known application devices, the individual components are fed from syringe bodies through channels to the discharge site of the device. In some of the known application devices, these channels extend through a head piece at whose side facing away from the syringe bodies, a multiple lumen tube is connected. This tube is arranged at a connection site of the head piece towards which (closely adjacent) the channels lead, which, in turn, start from the inlet side of the head piece facing away from the connection site. The connection devices (cones) for connecting the syringe bodies are also located on this inlet side.

In the case of the application device according to EP 0 315 222 B1, a four-lumen catheter is connected to the head piece. Two of the lumina of the catheter are used for transporting the components of the tissue adhesive, whereas a medical gas is fed through the third lumen. In the remaining fourth lumen, there is a metal wire which is plastically deformable (shaping wire). By manually bending the multiple lumen tube, the purposeful application of the adhesive at certain sites, particularly those difficult to access, is simplified. Naturally, the metal wire has a relatively high resistance force when it is subject to forces in axial direction. Hence, there is the danger that the multiple lumen tube does not immediately yield if it hits an obstacle in axial extension of the shaping wire. Further, there is the danger of blocking one or several of the lumina of the catheter, if the metal wire is bent excessively or with a too small bending radius.

In the device according to U.S. Pat. No. 4,874,368, the channels feeding the components are made of metal cannulas led through a common sleeve in parallel and closely adjacent. By manually bending this sleeve, the application of the adhesive at sites difficult to access can be simplified. There is a certain drawback, however, that the channels extending through the tubular body (metal cannulas with enclosing sleeve) are only conditionally flexible when the tubular body hits an obstacle.

SUMMARY OF THE INVENTION

It is the object of the present invention to provide an application device for multi-component products, particularly for medical tissue adhesives or dental adhesives, wherein the above-described drawbacks do not occur and which is sufficiently flexible when hitting obstacles, particularly when creating a tubular body which can easily be plastically deformed or bent.

In order to achieve this object, the invention provides a device for applying one or several fluids, particularly a multi-component fluid such as medical tissue adhesive or dental adhesive, which is provided with a head piece comprising channels for each fluid, which extend from an inlet side of the head piece to a connection site of the head piece, and a tubular body comprising an inlet end facing the connection site of the head piece and an outlet end facing away from the inlet end, there being further provided in the device of the invention an outer wall being configured, at least sectionally, such that the tubular body is plastically deformable, particularly plastically bendable.

In the device of the invention, the outer wall of the tubular body through which, starting from the head piece up to the discharge end of the tubular body, the individual components are, if necessary, transported by an additional medical gas, is configured to be at least sectionally plastically deformable, particularly plastically bendable. The tubular body, which preferably is made of a plastic material, accordingly does not have such a deflection resistant configuration and gives way when hitting obstacles, as may occur, e.g., when leading the application device to a site to be conglutinated. This characteristic of the application device of the invention is further supported when, for the purpose of separate transportation of the individual components to the discharge end of the tubular body, a flexible multiple lumen tube is led through this body. Then, the multiple lumen body is connected to the head piece at the connection site thereof and the tubular body encloses or surrounds the multiple lumen tube more or less tightly or with a certain radial clearance. The plastic deformability or bendability of the tubular body is chosen such that the elasticity of the multiple lumen tube does not result in an automatic resetting of the tubular body at its sections deformed by hand, for example.

The device of the invention comprises an at least sectionally plastically deformable, particularly plastically bendable tubular body. It is advantageous when plastically deformable portions of the tubular body and other non-deformable portions of the tubular body are arranged axially in succession. The tubular body which is suitably made of a plastic material and has only a very minor wall thickness (some few $\frac{1}{10}$ mm), is particularly deformable (kinkable) in the plastically non-deformable or non-bendable portions, but under the condition that this deformation need not absolutely be plastic, but may also be of elastic nature. By means of appropriate bending, the tubular body can be deformed into any shape and, particularly, it can also be returned into its original shape.

Advantageously, the outer wall of the tubular body is configured so as to be at least sectionally circumferentially folded in zigzag form, each such folded section comprising first radially inwardly directed and second radially outwardly directed wall sections. Seen in cross section through the outer wall of the tubular body, a first wall section and its neighbouring second wall section form a V, so that the entire folded section is configured in the manner of a bellows. The folded section described herein, however, differs from a conventional bellows in that the first and second wall sections have different axial lengths. Further, the first and second wall sections are connected to each other along circumferentially extending folding or kinking lines. In this manner, a flexible articulated section is formed in the tubular body, the articulacy of the tubular body being achieved by individual toggle or over-center joints each of which is formed by a first wall section and the one second wall section connected thereto. In the axially upset and unbent state of the tubular body, the first and second wall sections extend in a saw-toothed manner (seen in cross section through the outer wall of the tubular body). If the tubular body is now bent in the folded section area, the abutting wall sections are moved away from each other over a part of the periphery of the tubular body. The neighbouring first and second folded sections automatically move into their opened V-shaped positions, if they are moved beyond the "dead center" during bending. This automaticity of movement and also the resistance of this joint against a return movement is achieved by the high deflection resistance of the circumferentially extending wall sections, within the folded sections in particular. The manner of functioning and operating of the above-described folded section of the tubular body is principally known from drinking and suction tubules. For the first time, this invention proposes to employ such tubular bodies with articulated configuration for the transmission of the components of a medical tissue adhesive or dental adhesive and for the transmission of medical gases and/or generally for the transmission of fluids for the purpose of employing them with a multi-component product application device.

The feature of the plastic deformability of a tubular body dispensing a single-component or multi-component fluid provided according to the invention can be applied wherever the locally directed application of fluids is concerned. In particular, the use of the tubular body for receiving an elastic single-lumen or multiple lumen catheter is not intended to be restricted to the above-described tissue adhesive applicator which will be described in detail hereinafter, but it can be used wherever an elastic deformability of the catheter is desired.

Alternatively, the tubular body of the device according to the invention can consist of separate deflection-resistant rigid tube sections which are articulately interconnected. The friction of the separate tube sections articulately interconnected is chosen such that there is no automatic restoration of neighboring tube sections after a pivotal movement. Advantageously, each tube section has one end thereof provided with a partially spherical projection clampingly received in the respective other end of the neighboring tube section, which, for this purpose, has a corresponding configuration at this end and at least partially encloses the spherical projection. The spherical projection comprises a through hole arranged in axial prolongation of the passage of a tube section. In case that tube sections of the aforementioned kind are employed, it can also be thought of forming only a portion or portions of the tubular body of these tube sections and to configure the rest of the tubular body rigid or flexible in a way different from that above.

BRIEF DESCRIPTION OF THE DRAWINGS

The following is a detailed description of an embodiment of the invention with reference to the drawings, in which:

FIG. 2 is an inside view of the head piece with longitudinally cut conduits and connections, FIGS. 3 and 4 are illustrations of a sectionally flexible and plastically deformable tubular body in straight and in sectionally bent states, respectively, FIGS. 5 and 6 are illustrations of a tubular body being flexible and plastically deformable over its entire axial length in straight and bent states, respectively, and FIG. 7 is an alternative configuration for the flexible (plastically bendable) tubular body.

DETAILED DESCRIPTION OF THE INVENTION

Figure 1:
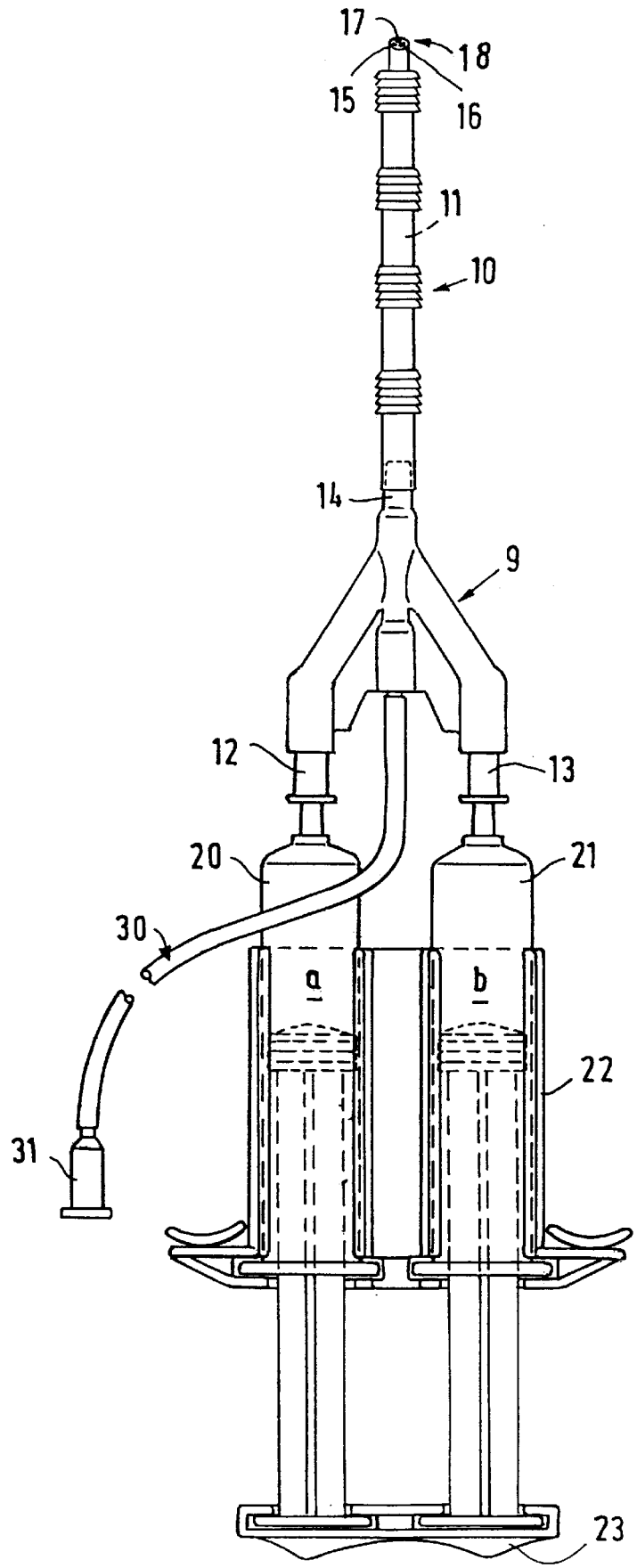
FIG. 1 is a top plan view of an application device.

The device for applying two-component products, such as medical tissue adhesives or dental adhesives, comprises a flat head piece 9 of plastics material at whose front end a tubular body 10 is arranged, which receives therethrough a multiple lumen tube 11. The tubular body 10 is affixed either to the head piece 9 or to the multiple lumen tube 11. The multiple lumen tube 11 is partially disposed in the head piece 9 (see inner portion 11a) and comprises an (outer) portion 11b protruding therefrom and being surrounded by the tubular body 10. From the rear end of the head piece 9, portions of two cannula hubs 12, 13 protrude. In top plan view, the head piece 9 is a triangular shape with the edges rounded. The multiple lumen tube 11 protrudes through an outer cone 14 of the head piece body and its inner portion 11a extends into the area of the front half of the head piece. The multiple lumen tube 11 has three lumina 15, 16 and 17 which extend in parallel from the inner end of the tube to the discharge end 18. The walls between the lumina 15, 16, 17 are extremely thin so that the lumina 15, 16, 17 lie very close together. The multiple lumen tube may be straight or bent according to a predetermined particular use. The length of the tubular body 10 and the portion 11b may be shortened by the user as desired. Two components a and b are contained in syringes 20, 21, the barrels of which are held together in a rack structure 22. The plunger rods of the syringes 20, 21 are coupled by a bridging member 23 such that both are operated simultaneously so that the components a and b enter the cannula hubs 12 and 13 at the same time.

The cannula hubs 12 and 13, partially included in the head piece 9, are connected to rigid cannulas 25, 26, preferably made of metal. Each metal cannula 25, 26 is cranked so that two legs 25a, 26a and 25b, 26b are obtained, the axes of which are parallel and which are connected by a longer inclined portion. The two metal cannulas 25, 26 are orientated in the head piece 9 such that they extend in V-shape. Firmly connected to the rear legs 25a, 26a are the cannula hubs 12, 13 that project beyond the edge of the head piece 9 by a part of their length. The shorter front legs 25b, 26b are respectively set into an associated lumen 15, 16 of the multiple lumen tube 11 which are provided for separately conducting the two components a, b. Firmly set into the third lumen 17 is an end of a connecting tubule 27, onto the other end of which a soft flexible air tube 30 is set. The connecting tubule 27 may be of metal or plastics material. The air tube 30 extends from the tip of the V formed by the two metal cannulas 25, 26 straight to the rear end of the head piece 9 and has a portion 30b leaving the same freely. The length of the portion 30b of the air tube 30 is at least about 10 cm. Its outer diameter may be about 2.5 mm. At the free outer end of the rear portion 30b, a connecting member 31 is provided in the form of a hub member for connection to an air conduit of an air aggregate. The coupling member 31 may be a female Luer lock cone to which an air filter set of the air aggregate may be coupled.

The metal cannulas 25, 26, the inner portion 11a of the multiple lumen tube 11 and the front portion 30a of the air tube 30, as well as the cannula hubs 12, 13 are moulded or injected into the head piece 9 of plastics material.

The air tube 30 is in direct communication with the lumen 17 of the multiple lumen tube 11 through the connecting tubule 27. The precise flows of the components a and b and the air flow emerge close together as a thin jet from the discharge end 18 of the multiple lumen tube 11. The components a and b are sprayed in an optimal mixture by the air flow so that the site to be treated is supplied with a sufficient quantity of dispersed tissue or dental adhesive of high quality. Due to the separate conduction of the components a and b and the air, the material is mixed only past the discharge end 18 of the multiple lumen tube 11. All channels, from the syringes 20, 21 to the discharge end 18, stay clear and maintain their original passage diameters, and no obstructions that could degrade the product quality at the discharge end will occur. Accordingly, the portions of the components a and b are dosed exactly and the composition of the adhesive is always correct.

As mentioned at the beginning of the description of the Figures, the multiple lumen tube 11b is surrounded by the sectionally flexible tubular body 10 consisting of extruded plastic material. According to FIG. 3, the tubular body 10 comprises folded sections 32 and straight sections 34, which are alternately arranged successively in axial extension of the tubular body 10. In the folded sections 32, the tubular body 10 is configured in the manner of a bellows and consists of zigzag-like arranged successive first and second circumferentially extending wall sections 36, 38. The wall sections 36, 38 are alternately arranged in succession and neighboring first and second wall sections 36, 38 are articulately interconnected along circumferentially extending kinking or folding lines or regions 40. The first wall sections 36 have a greater axial length than the second wall sections 38. In other words, the distance between two kinking regions 40 limiting a first wall section 36 is greater than in the case of a second wall section 38. In FIG. 3, the tubular body 10 is shown in its upset straight state, in which the first and second wall sections 36, 38 extend in mutual contact in saw-toothed manner, which is only shown conditionally in FIG. 3. By bending the tubular body 10 in the region of a folded section 32, the wall sections 36, 38 in that region of the outer wall of the tubular body 10, in which an axial extension of the outer wall occurs, are moved apart. The wall sections 36, 38 are moved away from each other, whereby a radial upsetting of the tubular body 10 occurs in the kinking regions 40 (when the neighboring wall sections 36, 38 start to move apart). When the neighboring wall sections 36, 38 move further apart, the tubular body 10 in turn relaxes in the kinking regions 40, so that the curvature shown in FIG. 4 for the two folded sections 32 is automatically maintained (plastic deformability). For without any action of force, the neighboring wall sections 36, 38 cannot return to their state of abutting all around according to FIG. 3, since this, in turn, is associated with an upsetting of the tubular body in the kinking regions 40 of the folded sections 32. The principle of kinkability of a tubular body by forming a plurality of closely successive snap joints in this manner is known, as described above and shown in the Figures, from drinking and suction tubules ("straw").

FIGS. 5 and 6 show an alternative of the tubular body 10. The tubular body 10' according to FIGS. 5 and 6 differs from the tubular body 10 in that its folded section 32' extends over the entire axial length. FIG. 6 shows the tubular body 10' kinked at three locations. Partially, the kinking directions are opposite to each other.

In the case of the application device for tissue adhesive, it is possible, as is shown in FIGS. 3 to 6, to give the multiple lumen tube 11 the desired course in order to be able to apply the tissue adhesive also to sites difficult to access. As a whole, the tubular body 10 or 10' remains sufficiently flexible to be able to yield when hitting an obstacle.

FIG. 7 shows—partially in side view and broken and in section, respectively—a modification of a tubular body 10" consisting of separate rigid tube sections 42 comprising passages 44 in mutual alignment through which the three-lumen catheter 11" extends. Neighboring tube sections 42 are coupled to each other by means of ball-and-socket joint-like connections. At one of its axial ends, each tube section 42 comprises a spherical formation 46 being clampingly embraced (in a snap connection-like manner) by the other end 48 of the respective neighboring tube section 42.

The clamping is selected such that the frictional force between neighboring tubular sections 42 being pivoted relative to each other prevents restoration of the tubular body 10" into the linearly extending state due to the elasticity of the catheter 11".

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A device for applying one or several fluids, at least one fluid, comprising:
   a head piece having a plurality of channels extending from an inlet side of the head piece to a connection site of the head piece, one of said plurality of channels corresponding to each of the at least one fluid to be applied,
   a tubular body including a plurality of tube sections clampingly and articulately interconnected, an outer wall, which, at least sectionally, is configured such that the tubular body is plastically deformable, an inlet end facing the connection site of the head piece, and an outlet end facing away from the inlet end,
   a flexible multiple lumen tube extending from the connection site of the head piece, said flexible multiple lumen tube having lumen aligned with said plurality of channels of the head piece, said flexible multiple lumen tube being disposed within the tubular body.

2. A device for applying at least one fluid, comprising:
   a head piece having a plurality of channels extending from an inlet side of the head piece to a connection site of the head piece, one of said plurality of channels corresponding to each of the at least one fluid to be applied.
   a tubular body, the tubular body having an inlet end facing the connection site of the head piece and an outlet end facing away from the inlet end, said tubular body including an outer wall, which, at least sectionally, is configured such that the tubular body is plastically deformable.
   a flexible multiple lumen tube extending from the connection site of the head piece, said flexible multiple lumen tube having lumen aligned with said plurality of channels of the head piece, said flexible multiple lumen tube being disposed within the tubular body, wherein
   the outer wall of the tubular body is at least sectionally configured so as to be circumferentially folded in a zigzag-like manner, and that each of said folded sections comprises first radially inwardly directed and second radially outwardly directed wall sections, which are alternately arranged in succession, the first and the second wall sections having different axial lengths, and the outer wall comprising circumferentially extending folding or kinking regions along the connections between the first and second wall sections.

3. The device according to claim 2, wherein adjacent said folded sections are separated by a smooth section of the outer wall of the tubular body.

4. The device according to claim 2, wherein the outer wall of the tubular body is configured as a folded section over the entire axial length of the tubular body.

5. (The device according to claim 1, wherein ball-and-socket joints interconnection of adjacent pairs of the tube sections.

6. The device according to one of claims 1 2, 3, 4, or 5 wherein the tubular body is formed from a polymer material.

* * * * *